United States Patent [19]
Weiss

[11] Patent Number: 5,858,666
[45] Date of Patent: Jan. 12, 1999

[54] APPARATUS AND METHOD OF DETECTION EMPLOYING AN AC FREQUENCY SENSOR ARRAY

[75] Inventor: Paul S. Weiss, Seattle, Wash.

[73] Assignees: Biotechnology Research and Development Corporation, Peoria, Ill.; The Penn State Research Foundation, University Park, Pa.

[21] Appl. No.: 697,871

[22] Filed: Aug. 29, 1996

[51] Int. Cl.⁶ .......................... C12Q 1/68; G01N 27/26; G01N 33/53; G01N 33/552

[52] U.S. Cl. .................................. 435/6; 435/5; 435/16; 435/7.1; 435/7.9; 435/287.1; 435/287.2; 204/400; 204/403; 436/527

[58] Field of Search ...................... 435/6, 5, 16, 7.1–7.9, 435/287.1, 287.2; 204/400, 403; 422/82.01, 82.02; 436/518, 524, 527

[56] References Cited

U.S. PATENT DOCUMENTS

| | | | |
|---|---|---|---|
| 4,905,701 | 3/1990 | Cornelius | 128/660 |
| 5,143,854 | 9/1992 | Pirrung et al. | 435/6 |
| 5,151,110 | 9/1992 | Bein et al. | 55/75 |
| 5,192,507 | 3/1993 | Taylor et al. | 422/68.1 |
| 5,324,633 | 6/1994 | Fodor et al. | 536/243 |
| 5,397,896 | 3/1995 | Weiss et al. | 250/306 |
| 5,412,087 | 5/1995 | McGall et al. | 435/6 |
| 5,445,934 | 8/1995 | Fodor et al. | 436/518 |
| 5,532,128 | 7/1996 | Eggers et al. | 435/16 |
| 5,656,428 | 8/1997 | McAllister et al. | |

FOREIGN PATENT DOCUMENTS

| | | |
|---|---|---|
| 0640832 | 3/1995 | European Pat. Off. |
| WO9210587 | 6/1992 | WIPO |
| WO9309668 | 5/1993 | WIPO |
| WO9317339 | 9/1993 | WIPO |
| WO9322680 | 11/1993 | WIPO |
| WO9511995 | 5/1995 | WIPO |
| WO9522058 | 8/1995 | WIPO |

OTHER PUBLICATIONS

International Search Report by the European Patent Office mailed Dec. 4, 1997.

*Primary Examiner*—W. Gary Jones
*Assistant Examiner*—Jeffrey Fredman
*Attorney, Agent, or Firm*—Majestic, Parsons, Siebert & Hsue

[57] ABSTRACT

A transducer for detecting biomolecules comprises a bottom and a top unit. The bottom unit has a set of parallel electrically conductive transmission lines thereon and probes attached to selected locations along each transmission line for binding with the target molecule. The top unit has thereon a second set of parallel transmission lines transverse to those on the bottom unit. By applying AC signals sequentially to the two sets of transmission lines, each of the probe locations at the intersection of the two transmission lines can be addressed and the response of the probe in an unfilled detector location or a complex formed by the probe and the target in a filled detector location can be measured. If the target has been labelled, than the label at each of the locations may also be detected. The device can also be used for measuring binding constants between the probe and the target and concentrations of target solutions.

31 Claims, 4 Drawing Sheets

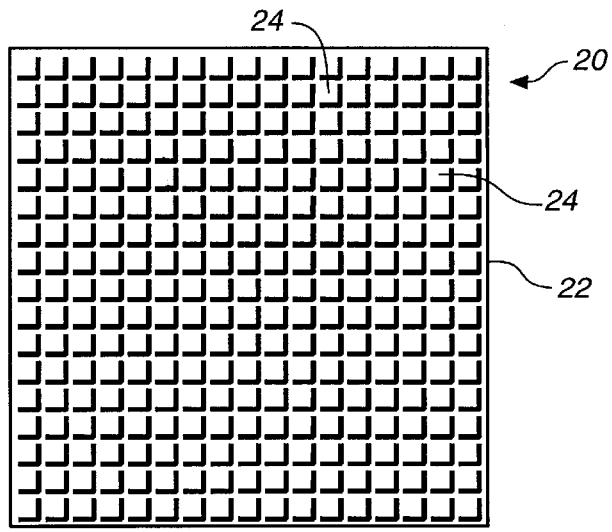
FIG._1
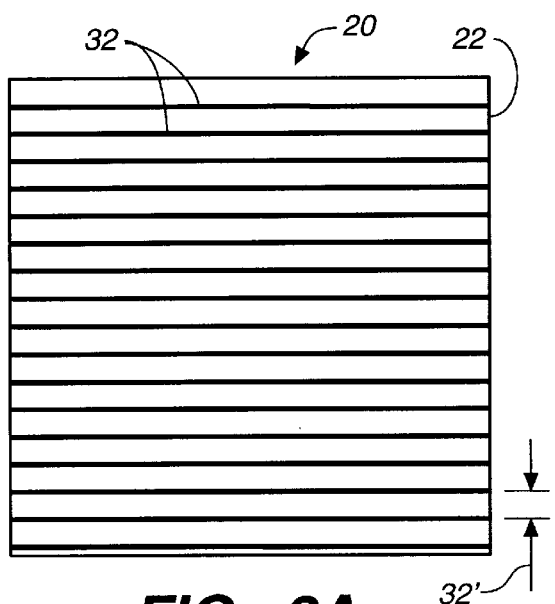
FIG._2A
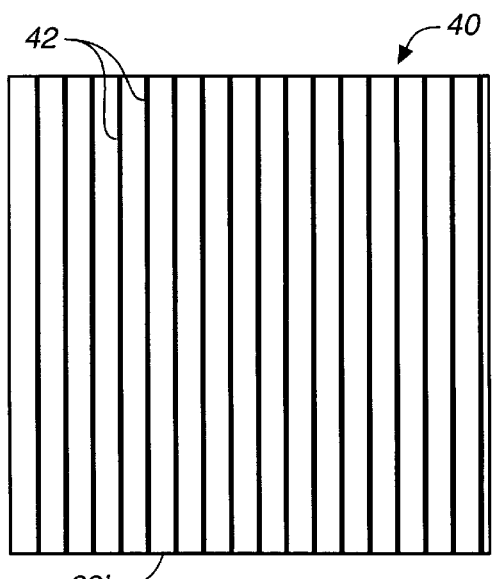
FIG._2B
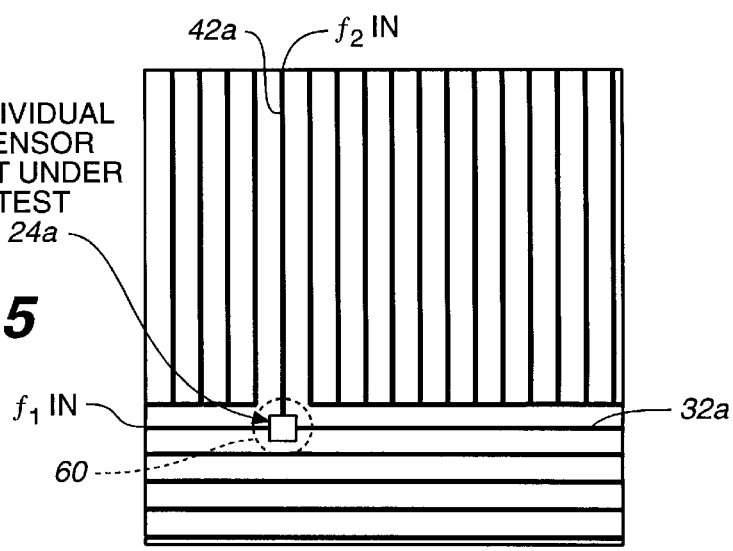
FIG._5

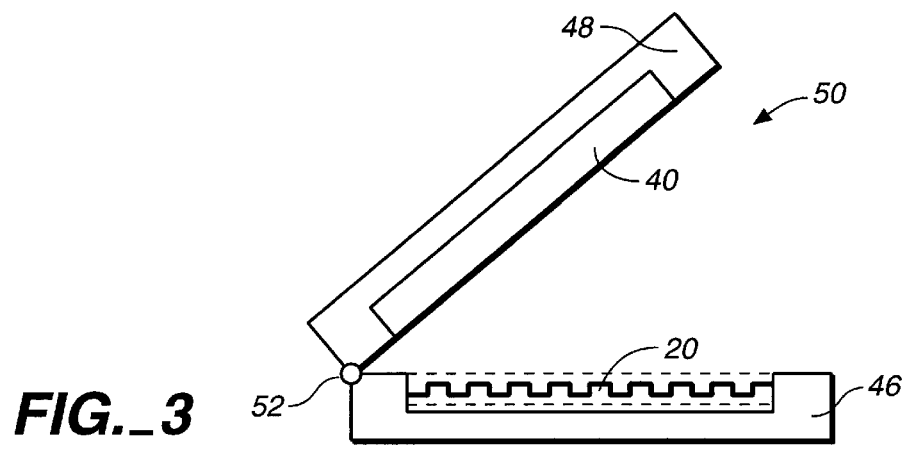
FIG._3
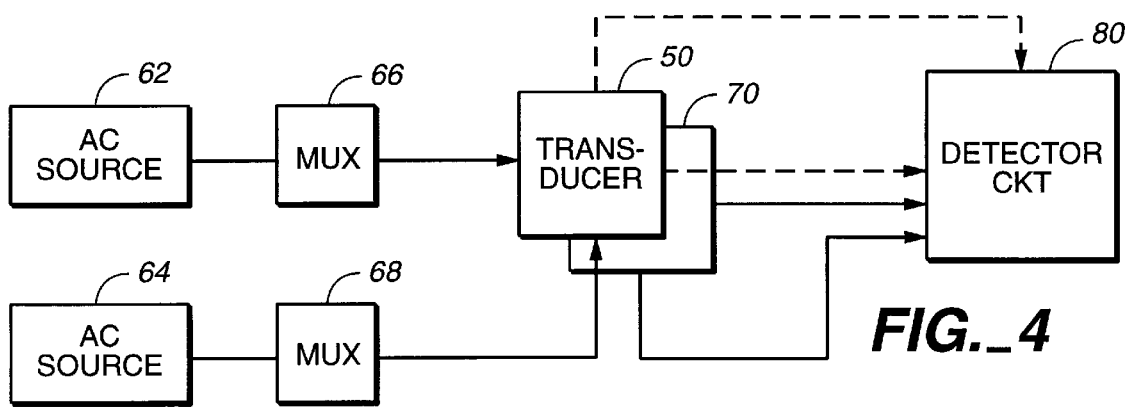
FIG._4
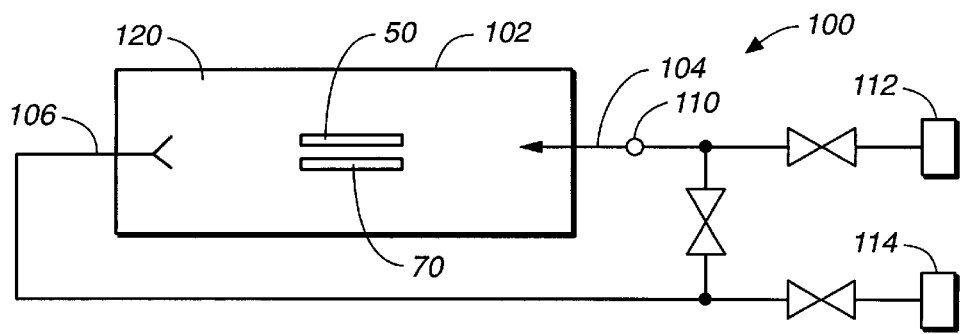
FIG._6

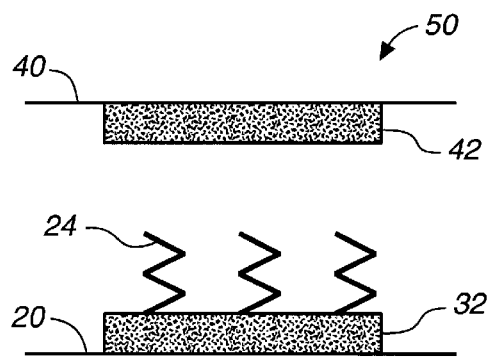
FIG._7
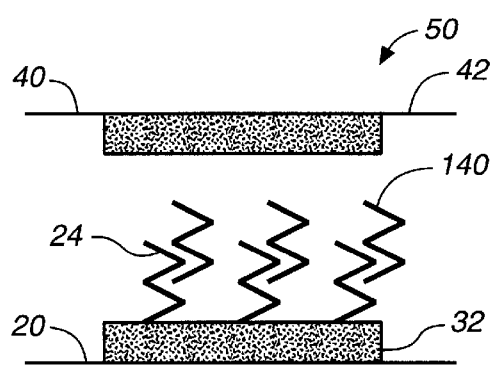
FIG._8
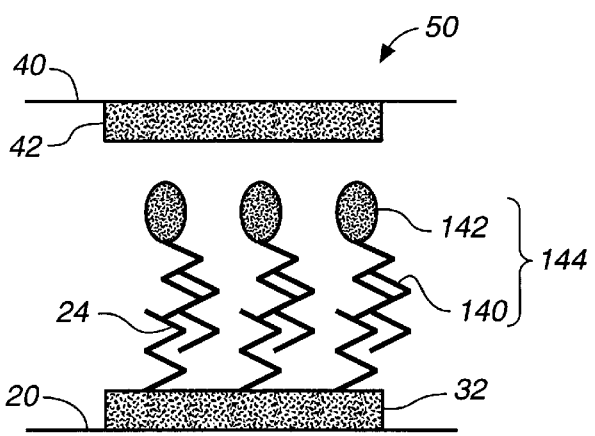
FIG._9
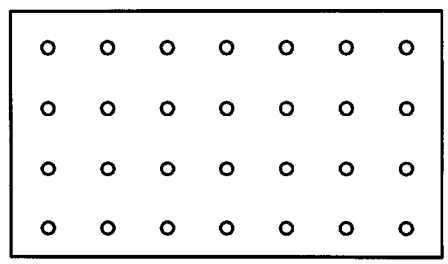
FIG._12

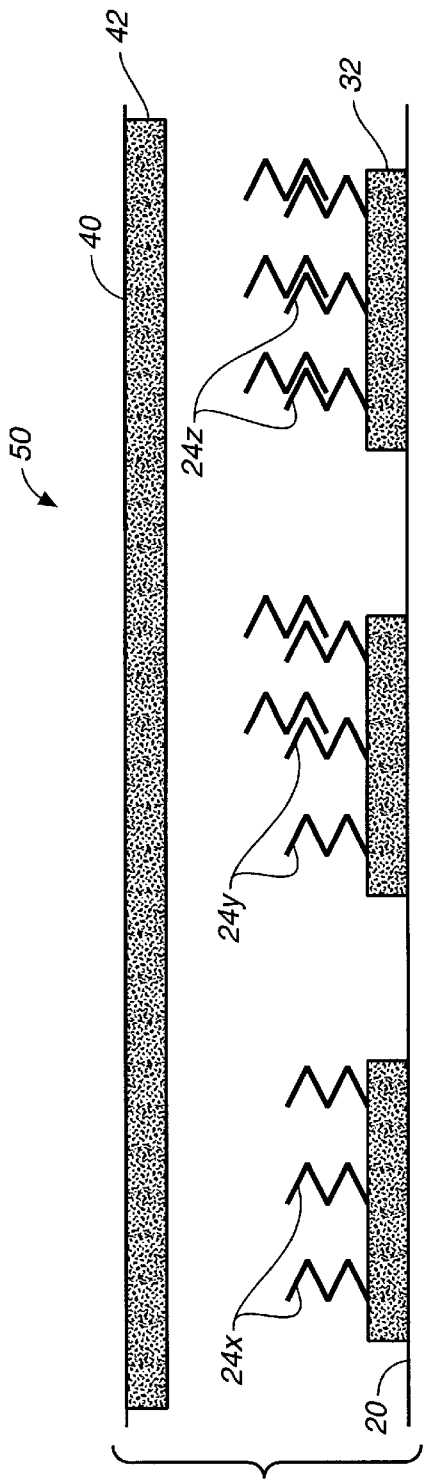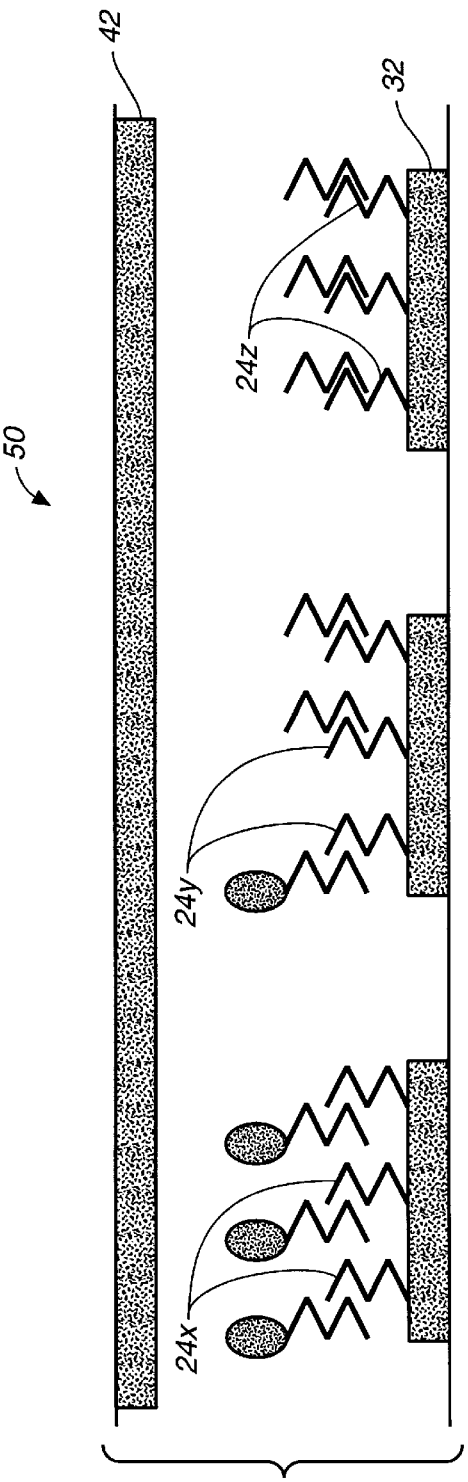

APPARATUS AND METHOD OF DETECTION EMPLOYING AN AC FREQUENCY SENSOR ARRAY

BACKGROUND OF THE INVENTION

The invention relates in general to techniques for detecting substances immobilized to a substrate, and in particular to a method and apparatus employing a sensor array operated at AC frequencies.

With the advent of the human genome project and other gene sequencing technologies, techniques for performing sequencing has been of great interest. There are many other medical, biological and analytical applications for sensor arrays. One sequencing technique involves the detection of fluorescently labelled materials, such as that described in U.S. Pat. No. 5,143,854. Such devices typically include a microscope and a monochromatic or polychromatic light source for directing light at a substrate. A photon counter detects fluorescence from the substrate, while an x-y translation stage varies the location of the substrate. A computer controls the movement of the x-y translation table and data collection. Light from the light source is focused at a substrate surface by manually adjusting the microscope. Manual adjustment may be time consuming and inconvenient. Furthermore, due to the inherent imperfections present in the x-y translation table and substrate, the substrate may be out of focus when it is moved by the table so that the data collected may be inaccurate.

Other devices for detecting fluorescently labelled materials employ charge coupled devices instead of microscopes. While such devices avoid the need for many adjustments of the microscope, such devices have limited resolution. In some sensor units available commercially, each sensor unit typically has dimensions of 20 microns by 20 microns.

It is therefore desirable to provide an improved technique for detecting immobilized substances on a substrate where the above-described difficulties and limitations are avoided.

SUMMARY OF THE INVENTION

One aspect of the invention is directed towards an apparatus for detecting a target, comprising a transducer having a two-dimensional array of detection locations; probes immobilized at sites that are at or close to the locations for combination with the target to form a complex; and means for applying AC electrical signals to the locations to detect said target.

Another aspect of the invention is directed towards a method for detecting a target, comprising the steps of: providing a transducer having a two-dimensional array of detection locations and probes immobilized at sites at or close to the locations for combination with the target to form a complex and causing said target to be at or close to at least one of the locations. The method further comprises applying AC electrical signals to said at least one of said locations and detecting an AC electrical signal at or close to said at least one of said locations to detect said target.

Yet another aspect of the invention is directed towards a method for making a transducer having a two-dimensional array of detection locations to detect a target. The method comprises the steps of immobilizing probes at sites at or close to the locations for combining with the target to form a complex having a characteristic frequency; determining said characteristic frequency and selecting a transducer for applying AC electrical signals at said locations, said transducer being adapted to transmit at said characteristic frequency.

BRIEF DESCRIPTION OF THE DRAWINGS

FIG. 1 is a top view of a portion of a transducer for detecting targets immobilized on a substrate to illustrate the preferred embodiment of the invention.

FIG. 2A and 2B are schematic views of horizontal and vertical transmission lines in the transducer of FIG. 1 to illustrate the preferred embodiment of the invention.

FIG. 3 is a cross-sectional view of the transducer of FIGS. 1, 2A, 2B showing two sets of transmission lines on respectively a top and a bottom portion that can be placed in close proximity to illustrate the preferred embodiment of the invention.

FIG. 4 is a schematic circuit diagram of an apparatus for detecting targets immobilized on a substrate to illustrate the preferred embodiment of the invention.

FIG. 5 is a schematic view to illustrate a process for addressing the transducer of FIGS. 1, 2A, 2B, 3 to illustrate the preferred embodiment of the invention.

FIG. 6 is a schematic view of a flow cell for causing a target substance to be in close proximity to a transducer and a detector to illustrate the preferred embodiment of the invention.

FIG. 7 is a schematic view of a transducer such as that of FIG. 1 with empty probes to illustrate the preferred embodiment of the invention.

FIG. 8 is a schematic view of a transducer such as that of FIG. 1 with filled probes to illustrate the preferred embodiment of the invention.

FIG. 9 is a schematic view of transducer such as that of FIG. 1 where the probes have been filled with tagged target substances.

FIG. 10 is a schematic view of the transducer of FIG. 1 employing a plurality of probes some of which are empty and some of which are filled to illustrate the preferred embodiment of the invention.

FIG. 11 is a schematic view of the transducer of FIG. 10 where the empty probes as shown in FIG. 10 have been filled with tagged target substances to illustrate the preferred embodiment of the invention.

FIG. 12 is a schematic view of the transducer of FIG. 1 employing a plurality of alternating current scanning tunneling microscope (ACSTM) sensor tips instead of two arrays of wires to illustrate an alternative embodiment of the invention.

For simplicity in description, identical components are labelled by the same numerals in the different figures of this application.

DETAILED DESCRIPTION OF THE PREFERRED EMBODIMENTS

The following terms are intended to have the following general meanings as they are used herein:

1. Complementary: Refers to the topological or chemical compatibility or matching together of interacting of a probe molecule and its target. Thus, the target and its probe, defined below, can be described as complementary, and, furthermore, the contact surface characteristics are complementary to each other.

2. Probe: A probe is a molecule or molecular complex that is recognized by a particular target. Examples of probes that can be investigated by this invention include, but are not restricted to, agonists and antagonists for cell membrane receptors, toxins and venoms, viral epitopes, hormones (e.g, opiates, steroids, etc.), hormone receptors, peptides, enzymes, enzyme substrates, cofactors, drugs, lectins, sugars, oligonucleotides, nucleic acids, oligosaccharides, proteins, and monoclonal antibodies.

3. Target: A target is a molecule that has an affinity for a given probe. Targets may be naturally-occurring in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells, or other materials), drugs, polynucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two molecules or molecular complexes have combined through molecular recognition to form a complex.

Applicant has discovered that, by employing a transducer that has a two-dimensional array of detection locations with probes immobilized at such locations, and by transmitting AC electrical signals to such locations, a target bound to one or more of the probes can be detected. In the preferred embodiment, the frequency of the AC electrical signal is tuned to a characteristic frequency of one of the probes, or of a complex formed by a target and a probe, so that the presence or absence of the target can be determined without using fluorescent or other labels. In the preferred embodiment, the AC signals are transmitted to the locations by means of two sets of intersecting transmission lines, where the spacing between adjacent lines in each set of lines is of the order of one micron or less so that the target can be detected at high resolution but without the disadvantages requiring the confocal microscopes or other optical means for detecting a fluorescently labelled target as in the above-described prior art systems.

FIG. 1 is a top view of a bottom portion 20 of a transducer, where portion 20 comprises a substrate 22 onto which a number of probes 24 have been attached for binding to the target to be detected. Probes 24 may be in the shape of elongated strands, such as strands of polymers (e.g. DNA), although symbolically, the probes have been shown as square blocks in FIG. 1. Not shown in FIG. 1 is a set of horizontal transmission lines shown in FIG. 2A. Thus, to construct the bottom unit 20 of the transducer, a set of horizontal transmission lines 32 are first fabricated on a substrate 22. Lines 32 are made of an electrically conductive material such as metal.

Transmission lines 32 are preferably parallel to one another, and so are lines 42 of FIG. 2B. In the preferred embodiment shown in FIGS. 2A, 2B, lines 32 are orthogonal to lines 42. It will be understood that this is not required and the lines 32 can simply be transverse to lines 42.

In the preferred embodiment, lines 32 may be made of gold and may be fabricated using masks and lithographic techniques commonly used in the semiconductor industry. The lines can also be fabricated using ink jet printing or other technologies. The spacing 32' between adjacent lines 32 can be made as small as required, by lithographic or other techniques used in the semiconductor or other industries. Then the probes 24 are attached to selected locations on the transmission lines 32. This may be accomplished as follows. First, linker molecules are attached to selected locations along one or more of the transmission lines 32. For example, thiol gold chemical techniques may be used to attach a probe to each linker molecular, such as an ω-functionalized alkane thiol, to form the probes 24 as shown in FIG. 1.

As shown in FIG. 1, probes 24 are attached at regular spacings along each of the horizontal transmission lines 32 to maximize the number of probes that can be attached to the substrate 22. Substrate 22 may be made of an electrically insulating and stable material such as glass or silica, or may be a metallic or semiconductor material with an insulating layer.

The top unit 40 of the transducer comprises a substrate 22' similar to substrate 22 and vertical transmission lines 42 fabricated on substrate 22' also using masks, lithographic techniques or ink jet printing or other techniques. The top and bottom units of the transducer can then be assembled together by means of a holder as shown in FIG. 3. FIG. 3 is a cross-sectional view of the transducer 50 comprising the top unit 40, the bottom unit 20 and the bottom holding portion 46 for holding the bottom unit 20 and a top holding portion 48 for holding the top unit 40. Portions 46, 48 may be connected by means of a hinge or alignment post 52 so that when the two portions are moved towards each other, the two units 20, 40 will be in close proximity to each other with the probes 24 lying between the horizontal and vertical transmission lines 32, 42. Portions 46, 48 can be made such that they permit passage of a fluid between the bottom and top units 20, 40. Alternatively, the top unit 40 can be made a part of the bottom unit by microfabrication techniques. In this case, hollows could be made between the horizontal and vertical transmission lines 32, 42.

The overall detection system is illustrated in FIG. 4. As shown in FIG. 4, the two sets of transmission lines 32, 34 are addressed respectively by two AC sources 62 and 64 respectively, through multiplexers 66, 68. In the preferred embodiment multiplexer 66 applies AC signals sequentially to one horizontal transmission line at a time in a scanning operation, scanning through all of the horizontal transmission lines one at a time. Multiplexer 68 is such that the AC signals from source 64 are applied sequentially to scan the vertical transmission lines 42, one at a time. Therefore, at any one time, electrical signals are applied on both sides of a probe only at the intersection of a vertical transmission line and a horizontal transmission line as illustrated in FIG. 5. As shown in FIG. 5, multiplexer 66 causes an AC signal of frequency $f_1$ to be applied sequentially to each one of the horizontal transmission lines 32, and multiplexer 68 causes an AC signal of frequency $f_2$ to be applied sequentially to each one of the vertical transmission lines 42. In FIG. 5, showing a particular instance in time in the scanning operation of both the horizontal and vertical sets of transmission lines, multiplexer 66 causes an AC signal of frequency $f_1$ to be applied to one of the horizontal transmission lines 32a, and multiplexer 68 causes an AC signal of frequency $f_2$ to be applied to one of the vertical transmission line 42a. Then, of all the probes 24, only the one 24a in between and overlapping the intersection of lines 32a, 42a will respond to and affect or change the signals applied to the two lines. Thus this particular probe that is being so tested is an individual sensor unit 60 at the intersection of transmission lines 32a, 42a as shown in FIG. 5, where all the remaining probes do not affect or respond to the signals applied. This is a particularly advantageous way for addressing a particular probe, and simplifies the construction and operation of the detection scheme.

In the case where there is some crosstalk between units, the largest effect still comes from probe 24a. The contributions from neighboring units 24 can be deconvoluted once they and their neighbors have been probed. Similarly for overwhelming signals due to crosstalk, duplication of substantially identical units with different neighbors in the transducer can be used to determine the presence or concentration of particular targets.

While the embodiment of FIGS. 1, 2A and 2B illustrates a transducer where the probes are attached to the bottom unit and not to the top unit, it will be understood that they can be attached to the top unit instead; such and other variations are within the scope of the invention. Instead of employing two separate substrates for supporting the two sets of transmission lines, it may be possible to support the two sets in a single substrate such as silicon. Such and other variations are within the scope of the invention. Where the substrates 22, 22' (or a single piece of semiconductor material substrate) are made of semiconductor material or a material on which semiconductors can be grown, it is also possible to fabricate the entire system in FIG. 4 on the substrates).

In reference to FIG. 5, the signals on the two transmission lines 32$a$, 42$a$ will mix so that if the frequencies $f_1$, $f_2$ themselves or any algebraic sum of or difference between them (given by the algebraic combination $Af_1+Bf_2$ where A, B may be zero or positive or negative integers) match (substantially equal to) the characteristic frequency of a probe or of a complex formed by a probe and a target or a label, such probe or complex or label will cause a change in the signal at the frequencies transmitted to the individual sensor unit 60. Such change in signal can be detected by means of a detector 70 in FIG. 4.

The detector 70 is preferably placed in close proximity to each of the individual sensor units to sense a change in signal and may comprise a solid piece of metal or a structure similar to that of detector 50 but without the probes. Since the addressing of a particular probe is accomplished by the two sets of transverse transmission lines, the construction of the detector can be less critical. The signals sensed by the detector 70 are then sent to a detector circuit 80 for analysis. In the preferred embodiment, the detector circuit may be a spectrum analyzer although a lock in amplifier or simply a filter may suffice in some situations. Detector 70 may be held in close proximity to transducer 50 by any suitable means, such as by clamping them together or by attaching them using an adhesive, or by fabricating them together. In some cases, transmission lines 32, 42 can serve as the detector.

FIG. 6 is a schematic view of a system for causing the target to bind to one or more of the probes. As shown in FIG. 6, system 100 includes a flow cell 102 having an inlet port 104 and an outlet port 106. A pump 110 pumps a fluid from storage 112 through the inlet port 104 to the flow cell 102. The fluid circulates through the flow cell and exits through the outlet port 106 to another storage 114.

The fluid 120 in flow cell 102 may contain a target that is to be detected or measured. When transducer 50 is placed in flow cell 102, the target that may be present in fluid may bind to one or more of the probes 24 in transducer 50. Then when AC signals are applied in the manner described above to individual sensor units 60 sequentially in the transducer 50, and if the probe in an unfilled sensor unit or the complex formed by the target and the probe in a filled sensor unit has a characteristic frequency that matches any one of the frequencies $f_1$, $f_2$ or a combination thereof, the probe or the complex will cause such frequency to change and the change of frequency is then detected by detector 70 and analyzed by detector circuit 80 for detecting the presence or absence of the target.

FIG. 7 is a cross-sectional view of a portion of the transducer 50 to illustrate the invention. As shown in FIG. 7, this portion of the transducer includes three probes 24 which are not bound to any targets. Therefore, if it is desired to detect the presence or absence of the target in a solution, for example, the frequencies of the AC sources 62, 64 may be tuned or set so that $f_1$ or $f_2$ or a combination thereof (referred to as detection frequency) matches the characteristic frequency of the probes 24 or that of a probe-target complex. It is possible to match a characteristic frequency much higher or lower than $f_1$, $f_2$ by using the sum or difference of $f_1$, $f_2$, or a combination of the two. This may be performed using a tuning process similar to that performed in ACSTM as described in U.S. Pat. No. 5,397,896. After the frequencies of the AC signals have been so tuned or set, such frequencies are applied to the transducer and the response or change in signal is measured. Then the transducer is placed in a flow cell 102 of FIG. 6 and the fluid to be tested is then injected through the inlet port 104 and adequate time is allowed for equilibrium to be reached within the flow cell between the probes and the fluid. Transducer 50 is then again measured at said tuned frequency to record any change in amplitude of the response detected by the detector 70. The detection frequencies may be in the range of about 1 Hz to 45 GHz.

Where the detection frequency matches the characteristic frequency of the probes 24, a reduction in the amplitude of the signal detected by the detector 70 compared to that prior to the transducer being exposed to the fluid to be tested will indicate the presence of the target substance of the fluid, whereas an absence of the target is indicated by the fact that there is little or no change in detector signal. If the number of probes 24 adapted for binding to the particular target in transducer 50 is known, or if the binding of the probes to the target has been calibrated, it may be possible to deduce the concentration of the target in the fluid to be tested from the above-described measurements.

FIG. 8 is a schematic view of a portion of transducer 50 where the probes 24 in this portion are bound to the target 140. In this instance, the AC signals delivered by sources 62, 64 may be tuned as before to the characteristic frequency of the complex formed by probe 24 and target 140. In this manner, detector 70 may be used to detect the presence or absence of the target in the fluid to be tested where a lack of change in signal will indicate the lack of target, while a change in signal will indicate its presence. The complex is formed again by placing the transducer in flow cell 102 and feeding the fluid to be tested into the flow cell as described above in reference to FIG. 7.

In some situations, the target to be detected may be of such a nature that it is difficult to detect a probe that will bind to it or to detect the complex formed by the probe and the target. In such circumstances, it may be desirable first to label the target 140 by means of a label 142 to yield a labelled target 144. The operator then has the choice of either detecting the presence of the labelled target 144 by having AC sources 62, 64 so that $f_1$, $f_2$ or a combination thereof matches the characteristic frequency of the complex formed by probe 24 and labelled target 144, or by simply detecting the label 142, which is more likely to be the case. In one embodiment, a labelled target 144 does not need to include the main target 140. It simply needs to be able to bind to the probe.

The scheme of this invention may also be used to detect the binding constant (affinity) and/or concentration of a particular target in a fluid. It is possible to use the above described transducer to measure the binding constants of the probe to the target and/or the concentration of the target substance. For example, a target solution of known concentration is first supplied to the transducer to reach equilibrium with the probes. AC signals are then transmitted to the probes and their complexes in the transducer in the manner described above to measure the responses at each of the locations of interest. Then a solution of the target at a higher known concentration than before is fed to the same transducer to again reach equilibrium with the probes and the response of the probes and complexes formed are again measured at the locations of interest in the manner described above. This process can be repeated further. A comparison of the two or more responses will yield the binding constants of the probes 24.

To increase the range of targets that can be detected, probes that bind to different targets may be employed in the same transducer. This is illustrated in FIGS. 10 and 11. As shown in FIG. 10, where the probes 24$x$, 24$y$, 24$z$ have the same binding constant or affinity for the target to be measured, then transducer 50 will function essentially in the same manner as that described above in reference to FIGS. 7–9 for detecting the presence or absence or the concentration of the target. However, the groups of probes such as 24$x$, 24$y$, 24$z$ may be made such that they have different affinities or binding constants to the target at issue. As shown in FIG. 10, probes 24$z$ has the highest affinity or binding constant to the target while probes 24$x$ do not significantly bind to the target at all while probes 24$y$ are somewhere in between. The process described above for measuring binding constants can then be used to yield the binding constants of the various different probes 24$x$, 24$y$, 24$z$. Once the binding constants of the probes for a particular target have been determined, the user can then determine the concentration of the target in a fluid by binding the target to the probes as described and measuring the response by transmitting AC signals thereto and measuring the response.

Alternatively, a qualitative indication of the relative affinity or binding constant of the different probes to a given target may be determined by feeding a solution containing the target to the transducer and measuring the response at each of the probes shown.

The configuration in FIGS. 10 and 11 may also be used for verification of results, where the probes 24$x$, 24$y$, 24$z$ have the same affinity for a particular target. The number of probe locations where target is bound in FIG. 10 may be counted in a first measurement. Then a fluid with an abundance of labelled target is caused to contact the unfilled probe locations to fill all the unfilled locations, and the number of locations with labelled targets are again counted in a second measurement to verify the accuracy of the first measurement if the total number of probe locations is known. Alternatively by counting the sites filled with labelled compounds, the number of sites where the unlabelled target is bound can be deduced.

The label 142 referred to above in FIG. 9 and in FIG. 11 may be a metallic material, such as a gold colloid which may be attached to the target by means of thiol gold chemistry or streptavidin biotin or other methods known to those skilled in the art.

In the construction of the above-described transducer 50 in FIGS. 1, 2A and 2B, it is desirable for the transmission lines 32, 42 to be suitable for transmitting the AC signals of the desired frequencies. For this purpose, it may be desirable first to determine the characteristic frequency of the substance to be detected, such as the characteristic frequencies of one or more different probes, complexes formed by the probes and targets, or complexes formed by probes and labelled targets. A characteristic frequency of a probe, or a complex of the type referred to above can be determined by means of an ACSTM in the manner such as that described in U.S. Pat. No. 5,397,896. If metal particles are used for labelling the target, tuning is less of an issue since the metallic label will cause a strong response irrespective of the frequency of the AC signal on the transmission lines.

In case there are variations in the characteristics of probes 24, it may be desirable to determine a standard threshold for the probes. This can be done by comparing the responses at or close to two sites where similar probes are located when AC signals are applied to the two sites. Then the threshold is applied to the response detected at the same or other locations.

Instead of using sets of parallel transmission wires or other elongated conductors as in FIGS. 2A, 2B, a two-dimensional array of electrically conductive probes may be employed instead where each of the probes will function in the same manner as that of an ACSTM for transmitting and/or for detecting signals. Such an embodiment is illustrated in FIG. 12. For such a transducer, a single AC source instead of two sources will be adequate when used with a single multiplexer for applying the AC signals sequentially to each of the electrically conductive probe tips of the two-dimensional array of probes. The above probe tips can be placed on transmission lines 32 and/or 42 on one or both sides of the device. Addressing is still at the probed unit 24$a$ by applying AC frequencies to transmission lines 32$a$, 42$a$, but the signal is enhanced by the use of these microfabricated probe tips.

The embodiment of FIGS. 2B and 2C is advantageous over that of FIG. 12 since it greatly simplifies the construction of the transducer. Since each probe location can be addressed by the intersection of a horizontal and a vertical transmission line, only 2,000 transmission lines will be adequate for addressing a total of one million intersection probe locations. Furthermore, with the state of the art semiconductor fabrication technology, the spacing between adjacent lines can be as small as one micron or less, so that a one square centimeter transducer can accommodate about one million probe locations for detection. The transducer of FIGS. 2A and 2B and 12 are also advantageous since there are no moving parts, in contrast to the devices for detecting fluorescently labelled molecules employing microscopes. These devices are also advantageous over prior art fluorescent based detection systems employing charge coupled devices because of the superior resolution that can be achieved by this invention.

While the invention has been described above by reference to various embodiments, it will be understood that modifications and changes may be made without departing from the scope of the invention which is to be defined only by the appended claims and their equivalents.

What is claimed is:

1. An apparatus for detecting a target, comprising:
   a transducer having a two dimensional array of locations;
   probes immobilized at sites substantially at the locations for combination with the target to form a complex, said probe, target or complex having a characteristic frequency which identifies said probe, target or complex;
   means for applying AC electrical signals of selected frequency or frequencies to the locations; and
   means for detecting said target at said locations by detecting a change in the signals at the selected frequency or frequencies.

2. The apparatus of claim 1, said transducer comprising a first and a second array of elongated electrical conductors, said two arrays arranged transverse to one another, the conductors in the first array overlapping those in the second array so that the probes are in between and/or at intersections of overlapping conductors.

3. The apparatus of claim 2, said means for applying comprising a circuit for applying a first AC electrical signal sequentially to the first array of elongated electrical conductors, and a second AC electrical signal sequentially to the second array of elongated electrical conductors.

4. The apparatus of claim 1, said detecting means comprising a first and a second array of electrical conductors, said two arrays arranged transverse to one another, the conductors in the first array overlapping those in the second array.

5. The apparatus of claim 3, wherein the first and second AC electrical signals have different frequencies, so that one of said different frequencies or a combination of the different frequencies matches the characteristic frequency that identifies a probe or a complex including the target and a probe.

6. The apparatus of claim 1, wherein at least two of said probes substantially at two different locations are adapted to bind to different targets.

7. The apparatus of claim 1, said transducer comprising a two dimensional array of sensor tips at said two dimensional array of locations.

8. The apparatus of claim 1, wherein a complex of the target with one of the probes has one or more characteristic frequencies which identify the complex, said applying means applying electrical signals of such frequencies to one or more locations in the array that the frequencies or a combination thereof are substantially equal to said characteristic frequencies.

9. The apparatus of claim 1, said detecting means including a filter, lock in amplifier or spectrum analyzer connected to the transducer.

10. The apparatus of claim 1, said detecting means including a detector having a two dimensional array of detection locations, and a sensing range for each of said detection locations, said locations being at or within sensing range(s) of the two dimensional array of detection locations.

11. The apparatus of claim 10, said detecting means further including a filter, lock in amplifier or spectrum analyzer connected to the detector.

12. The apparatus of claim 1, wherein the probes substantially at at least two of said locations have affinity for the same target.

13. The apparatus of claim 1, wherein the target has been tagged with a label to form a complex, said complex or said label having one or more characteristic frequencies which identify the complex, said frequency or frequencies, or a combination thereof, of said AC signals applied by the applying means being substantially equal to the one or more characteristic frequencies of said complex or said label.

14. The apparatus of claim 1, said selected frequencies being in the range of about 1 Hz to 45 GHz.

15. The apparatus of claim 1, wherein said probes have different binding constants to a target.

16. A method for detecting a target or a target labelled with a label, comprising the steps of:
providing a transducer having a two dimensional array of locations and probes immobilized at sites substantially at the locations for combination with the target or the labelled target to form a complex, at least one of said probes, said target, said label, said labelled target or said complex having one or more characteristic frequencies which identify the probe, target, label, labelled target or complex;
providing said target or said labelled target to at least one of said locations;
applying AC electrical signals of a selected frequency or frequencies to said at least one of said locations; and
detecting an AC electrical signal at or within sensing range of said at least one of said locations to detect said target or labelled target.

17. The method of claim 16, wherein said frequency or frequencies applied in the applying step, or a combination thereof, are substantially equal to the one or more characteristic frequencies which identify said at least one of said probes, said target, said label, said labelled target, or said complex.

18. The method of claim 17, said applying step applying AC electrical signals sequentially to a plurality of the locations, said detecting step detecting AC signals at said plurality of locations substantially at or within sensing range of a detector to determine the concentration of the target.

19. The method of claim 18, wherein not all the probes are bound to the target, said method further comprising:
providing a labelled material to the probes not bound to the target; and
detecting the concentration of the labelled material to deduce the concentration or the presence of the target.

20. The method of claim 17, further comprising:
providing sequentially targets of at least two different concentrations to the probes; and
wherein said detecting step detects AC signals at said probes each time after targets at each of the at least two concentrations have been provided to the probes to determine the binding or affinity constant of the target with said probe.

21. The method of claim 20, wherein not all the probes are bound to the target after the providing step, said method further comprising:
providing a labelled material to the probes not bound to a target; and
detecting the concentration of the labelled material to deduce the concentration or the presence of the target.

22. The method of claim 16, wherein not all the probes are bound to a target, said applying step applying AC electrical signals to detect a labelled material, said method further comprising:
providing a labelled material to the probes not bound to the target; and
wherein said detecting step detects the concentration of the labelled material to deduce the concentration of the target.

23. The method of claim 16, wherein not all the probes are bound to a target, said method further comprising:
labelling the targets with labels to form labelled targets;
providing said labelled targets to at least one probe not bound to a target;
wherein said applying step applies AC electrical signals to detect a labelled target;
wherein said detecting step detects the labelled target to deduce the binding or affinity constant of the target.

24. The method of claim 16, said transducer comprising a first and a second array of elongated electrical conductors, said two arrays arranged transverse to one another, the conductors in the first array overlapping those in the second array at said two dimensional array of locations, said applying step applying a first AC electrical signal sequentially to the first array of elongated electrical conductors, and a second AC electrical signal sequentially to the second array of elongated electrical conductors to address the locations.

25. The method of claim 24, wherein said detecting step detects an AC electrical signal at or within sensing range of a detector at a detection location.

26. The method of claim 16, said transducer comprising a two dimensional array of sensor tips at said two dimensional array of locations, wherein said applying step applies signals sequentially to the array of sensor tips.

27. The method of claim 16, further comprising applying a threshold to the AC signal detected at or within sensing range of a detector from said at least one location.

28. The method of claim 27, said detecting step detecting AC signals at or within sensing range of a detector from at least two of said locations, said method further comprising comparing the AC signals detected and deriving said threshold.

29. The method of claim 16, said selected frequencies being in the range of about 1 Hz to 45 GHz.

30. A method for making a transducer having a two dimensional array of locations to detect a target or a target labelled with a label, comprising the steps of:
    immobilizing probes at sites substantially at the locations for combining with the target or the labelled target to form a complex, said probes, said target, said label, said labelled target or said complex having one or more characteristic frequencies which identify said probes, target, label, labelled target or complex;
    determining said characteristic frequencies;
    selecting a transducer for applying AC electrical signals at said locations, said transducer being adapted to transmit at said one or more characteristic frequencies or a combination thereof.

31. The method of claim 30, said determining step employing an ACSTM.

\* \* \* \* \*